US011382498B2

(12) United States Patent
Kitamura

(10) Patent No.: US 11,382,498 B2
(45) Date of Patent: Jul. 12, 2022

(54) OPHTHALMOLOGIC APPARATUS AND MEASUREMENT METHOD OF EYE

(71) Applicant: TOPCON CORPORATION, Tokyo (JP)

(72) Inventor: Kazuo Kitamura, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 497 days.

(21) Appl. No.: 16/437,233

(22) Filed: Jun. 11, 2019

(65) Prior Publication Data
US 2019/0380571 A1 Dec. 19, 2019

(30) Foreign Application Priority Data

Jun. 15, 2018 (JP) .............................. JP2018-114359

(51) Int. Cl.
A61B 3/00 (2006.01)
G06T 7/73 (2017.01)
(Continued)

(52) U.S. Cl.
CPC .......... A61B 3/0025 (2013.01); A61B 3/0033 (2013.01); A61B 3/0058 (2013.01);
(Continued)

(58) Field of Classification Search
CPC ... A61B 3/0025; A61B 3/0033; A61B 3/0058; A61B 3/117; A61B 3/14; A61B 3/107;
(Continued)

(56) References Cited

U.S. PATENT DOCUMENTS 5,557,350 A 9/1996 Yano
2001/0024265 A1 9/2001 Fujieda
(Continued)

FOREIGN PATENT DOCUMENTS

CN 1989894 7/2007
CN 104224110 12/2014
(Continued)

OTHER PUBLICATIONS

Extended European Search Report dated Oct. 16, 2019 in corresponding European Patent Application No. 19179400.7.
(Continued)

Primary Examiner — Mohammed A Hasan
(74) Attorney, Agent, or Firm — Wenderoth, Lind & Ponack, L.L.P.

(57) ABSTRACT

An ophthalmologic apparatus includes a measurement optical system to acquire information of an eye, an image obtaining part to obtain an anterior ocular segment image of the eye on an optical axis of the measurement optical system, a display to display the anterior ocular segment image, cameras to each capture an image of an anterior ocular segment of the eye from a different direction, a driving mechanism to move the measurement optical system in a vertical direction and a horizontal direction, and a controller. The controller is configured to acquire three-dimensional position information of the eye based on the images captured by the cameras and calculate moving amounts in the vertical and horizontal directions of the measurement optical system based on the three-dimensional position information. The controller is configured to display the anterior ocular segment image on the display while positioning the measurement optical system with the driving mechanism.

12 Claims, 11 Drawing Sheets

(51) Int. Cl.
*A61B 3/117* (2006.01)
*A61B 3/14* (2006.01)

(52) U.S. Cl.
CPC ............... *A61B 3/117* (2013.01); *A61B 3/14* (2013.01); *G06T 7/73* (2017.01); *G06T 2207/10028* (2013.01); *G06T 2207/20221* (2013.01); *G06T 2207/30041* (2013.01)

(58) Field of Classification Search
CPC . A61B 3/152; G06T 7/73; G06T 2207/10028; G06T 2207/20221; G06T 2207/30041
USPC ........................................................ 351/208
See application file for complete search history.

(56) References Cited

U.S. PATENT DOCUMENTS

| | | | |
|---|---|---|---|
| 2004/0044333 A1* | 3/2004 | Sugiura | A61F 9/00804 606/4 |
| 2007/0146636 A1 | 6/2007 | Ishikura | |
| 2007/0236660 A1* | 10/2007 | Fukuma | A61B 3/102 351/205 |
| 2013/0162946 A1 | 6/2013 | Dobashi et al. | |
| 2013/0188138 A1* | 7/2013 | Iwase | A61B 3/0025 351/206 |
| 2014/0300866 A1* | 10/2014 | Fukuma | A61B 3/0058 351/208 |
| 2014/0368791 A1 | 12/2014 | Kamada | |
| 2015/0085252 A1* | 3/2015 | Fujimura | A61B 3/0058 351/208 |
| 2016/0345822 A1 | 12/2016 | Fujimura et al. | |
| 2017/0055830 A1* | 3/2017 | Kotoku | A61B 3/0025 |
| 2017/0065174 A1* | 3/2017 | Yamamoto | A61B 3/16 |

FOREIGN PATENT DOCUMENTS

| | | |
|---|---|---|
| CN | 106821303 | 6/2017 |
| CN | 106963336 | 7/2017 |
| EP | 2 786 699 | 10/2014 |
| JP | 7-284475 | 10/1995 |
| JP | 8-103414 | 4/1996 |
| JP | 2013-248376 | 12/2013 |
| JP | 2014-200678 | 10/2014 |
| JP | 2017-51213 | 3/2017 |
| JP | 2017-176657 | 10/2017 |

OTHER PUBLICATIONS

Office Action dated Jun. 16, 2021 in corresponding Chinese Patent Application No. 201910520509.1, with partial English translation.
Notice of Reasons for Refusal dated Apr. 19, 2022 in Japanese Patent Application No. 2018-114359, with Machine Translation.

* cited by examiner

OPHTHALMOLOGIC APPARATUS AND MEASUREMENT METHOD OF EYE

CROSS-REFERENCE TO RELATED APPLICATION

The present application is based on and claims a priority benefit of Japanese patent application No. 2018-114359, filed on Jun. 15, 2018, the disclosure of which is hereby incorporated herein by reference in its entirety.

BACKGROUND

Technical Field

The disclosure relates to an ophthalmologic apparatus and a measurement method of an eye to be examined.

JP2013-248376A and JP2014-200678A exemplarily teach ophthalmologic apparatuses. The ophthalmologic apparatus of JP2013-248376A and JP2014-200678A images an anterior ocular segment of an eye to be examined with two or more of imaging parts such as cameras, and performs alignment of the eye to be examined with the measurement optical system based on the images acquired by the two or more of imaging parts.

The ophthalmologic apparatus of JP2013-248376A analyzes the two or more of captured images to determine a feature point such as a pupil center, and moves a main body of the apparatus in X, Y, and/or Z directions based on a position of the feature point and a three-dimensional position of the eye to be examined. The three-dimensional position of the eye is determined based on the positions of the two or more of the imaging parts. With this, the alignment/positioning of the measurement optical system with respect to the eye is adequately achieved.

JP2014-200678A additionally teaches a method to determine a three-dimensional position of an eye to be examined. The method of JP2014-200678A comprises steps of capturing two or more of images of an eye to be examined from different directions, extracting a partial image from the two or more of images, defining a position other than a pupil center as a feature point based on a composite image generated by the two or more of images, and determining the three-dimensional position of the eye. When an eye to be examined is, for example, a cataract eye, it is difficult to determine its pupil center. However, with the method of JP2014-200678A, it is possible to align/position the measurement optical system with respect to the eye.

With the conventional technologies, the examiner visually checks the captured image or the composite image displayed on a display in order to confirm the automatic alignment or in order to manually align/position the measurement optical system. Though, a technology capable of detailed confirmation of the alignment/positioning of the measurement optical system and of detailed observation of the status of the eye to be examined is even preferable so as to allow the examiner to accurately align/position the measurement optical system and to determine characteristics of the eye.

SUMMARY

An object of the disclosure is, therefore, to provide an ophthalmologic apparatus that allows an examiner to promptly and accurately align/position the measurement optical system by explicitly confirming alignment/positioning of a measurement optical system with respect to an eye to be examined and/or a status of the eye to appropriately determine characteristics of the eye.

In order to achieve the above object, an aspect of the present disclosure provides an ophthalmologic apparatus that comprises a measurement optical system configured to acquire information of an eye to be examined, an image obtaining part configured to obtain an anterior ocular segment image of the eye on an optical axis of the measurement optical system, a display configured to display the obtained anterior ocular segment image, two or more of cameras that each captures an image of an anterior ocular segment of the eye from a different direction, a driving mechanism configured to move the measurement optical system in a vertical direction and a horizontal direction, and a controller. The controller acquires three-dimensional position information of the eye based on the two or more of images captured by the two or more of the cameras and calculates a moving amount of the measurement optical system in the vertical direction and a moving amount of the measurement optical system in the horizontal direction based on the acquired position information. The controller then controls the driving mechanism based on the calculated moving amounts to position the measurement optical system with respect to the eye, and displays the obtained anterior ocular segment image on the display while positioning the measurement optical system.

Another aspect of the present disclosure provides a measurement method of an eye to be examined. The method comprises the following steps: obtaining an anterior ocular segment image of the eye on an optical axis of a measurement optical system; capturing two or more of images of an anterior ocular segment of the eye with two or more of cameras from different directions; acquiring three-dimensional position information of the eye based on the two or more of the captured images; calculating a moving amount of the measurement optical system in the vertical direction and a moving amount of the measurement optical system in the horizontal direction based on the acquired position information; positioning the measurement optical system with respect to the eye based on the calculated moving amounts; and displaying the obtained anterior ocular segment image on a display while positioning the measurement optical system.

DETAILED DESCRIPTION

Figure 1:
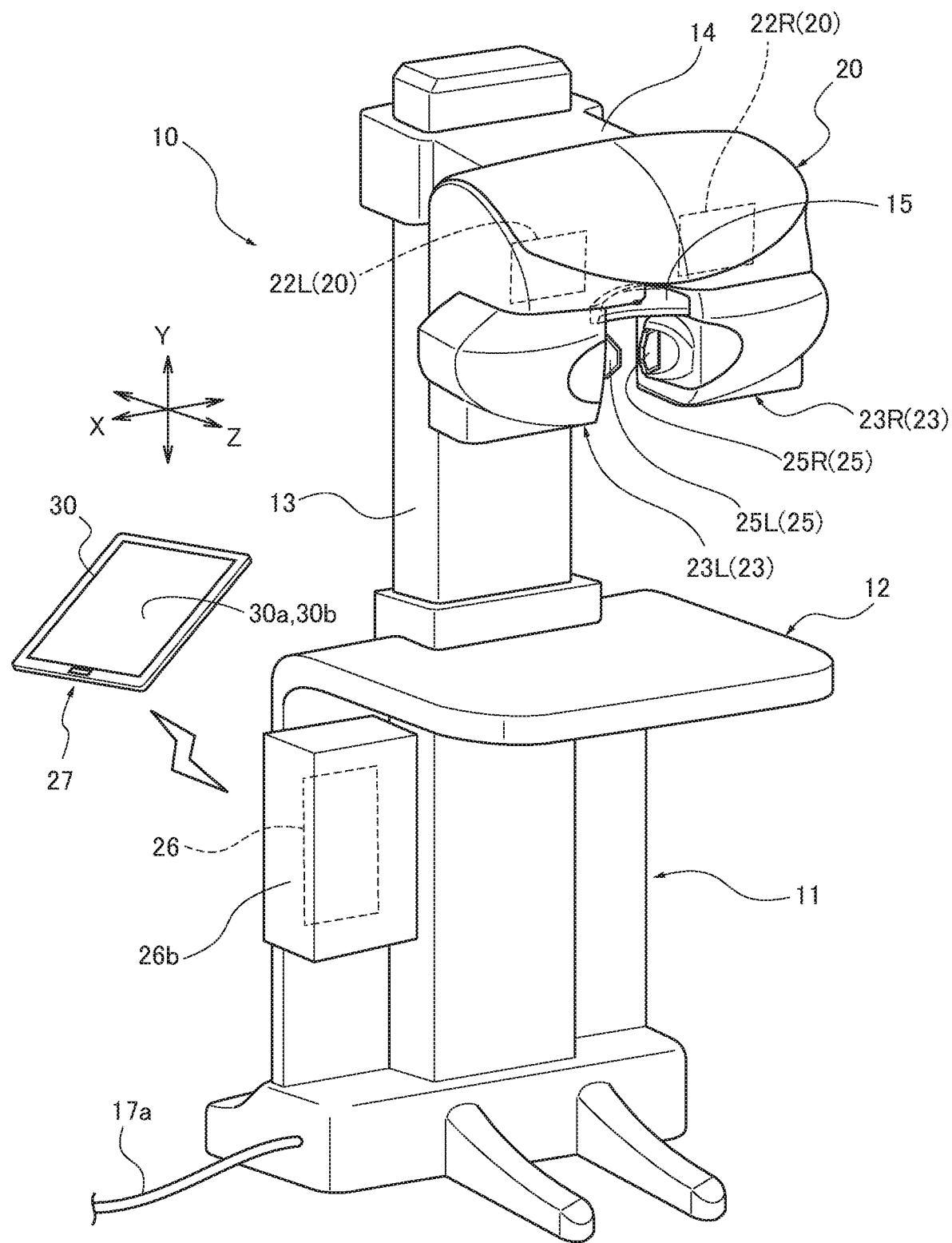
FIG. 1 is a perspective view illustrating an overall appearance of an ophthalmologic apparatus according to an embodiment.
Figure 2:
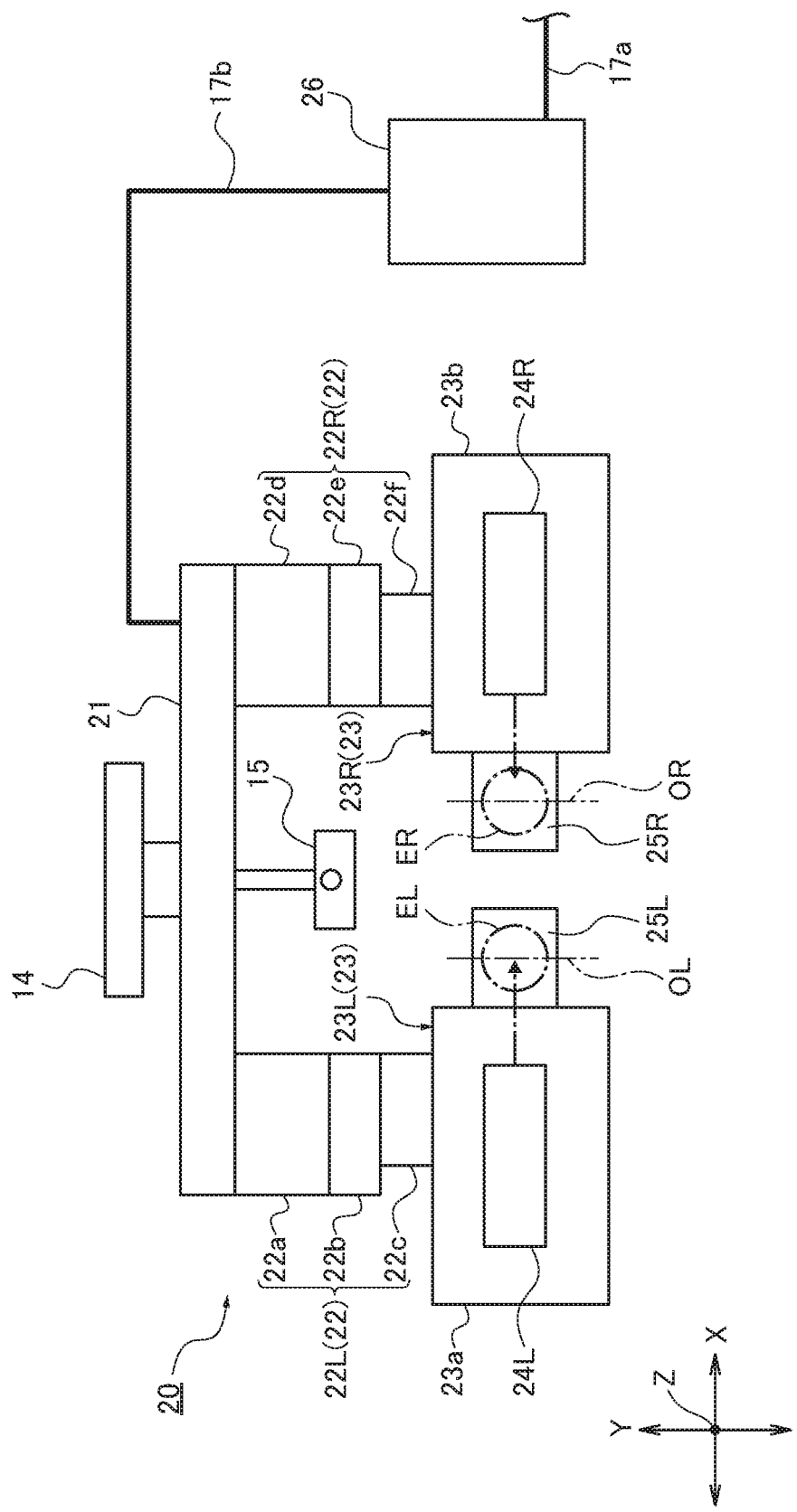
FIG. 2 is a schematic view illustrating a measurement unit of the ophthalmologic apparatus according to the embodiment.
Figure 3:
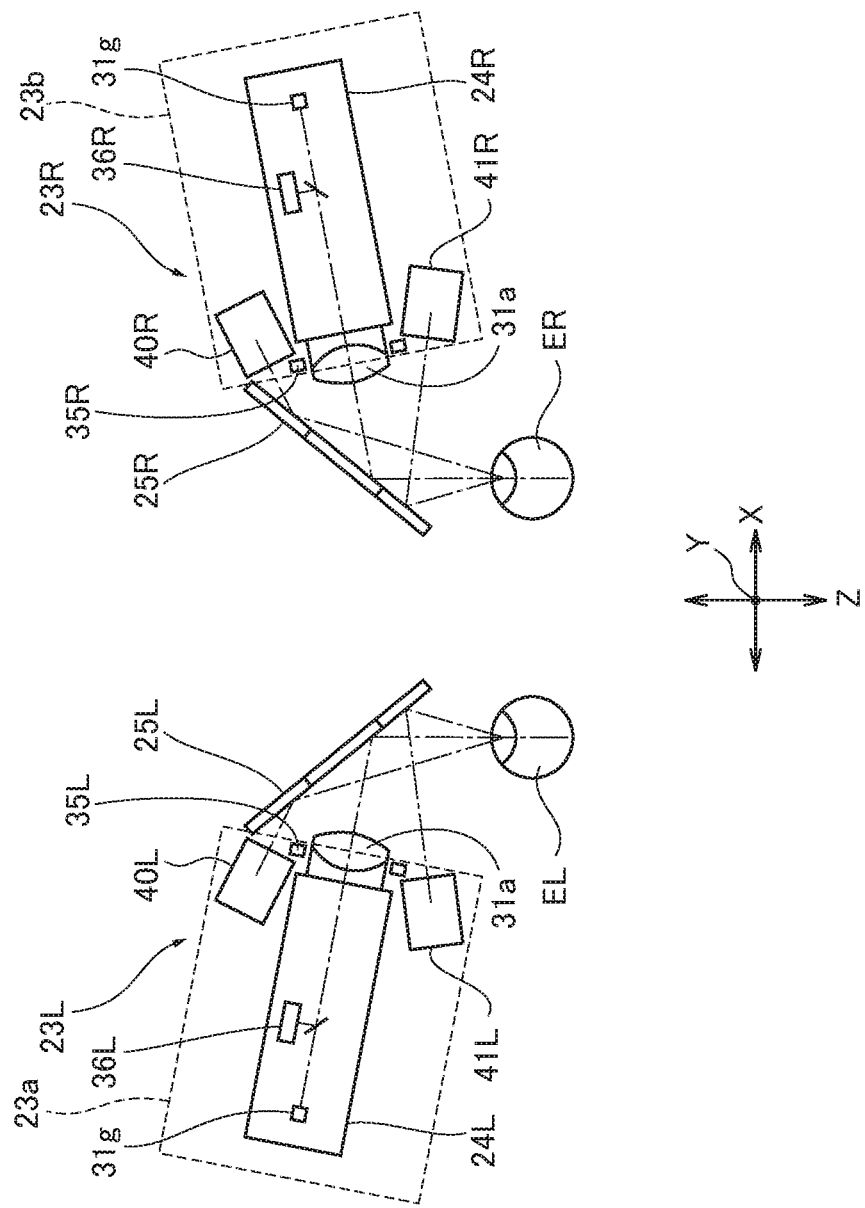
FIG. 3 is a schematic view illustrating a measurement optical system of the ophthalmologic apparatus according to the embodiment.

Hereinafter, an embodiment of an ophthalmologic apparatus according to this disclosure will be described with reference to the drawings. FIGS. 1-3 show an overall configuration of an ophthalmologic apparatus 10 according to the embodiment. The ophthalmologic apparatus 10 is a binocular ophthalmologic apparatus, which is capable of measurement with both eyes open such that the characteristics of the both eyes are measured simultaneously. It should however be noted that the ophthalmologic apparatus 10 of this disclosure is not limited to a binocular ophthalmologic apparatus and is also applicable to a monocular ophthalmologic apparatus.

The ophthalmologic apparatus 10 includes a base 11 installed on a floor, a table 12, a column 13, an arm 14 as a supporter, and a measurement unit 20, as shown in FIG. 1. With the ophthalmologic apparatus 10, a patient stands or sits in front of the table 12 and puts his/her forehead on a forehead rest 15 of the measurement unit 20 to measure characteristics of an eye to be examined. In this description, "X direction" means the left-and-right direction seen from the patient, "Y direction" means the vertical direction, and "Z direction" means the depth direction of the measurement unit 20 or the forth-and-back direction of the patient.

The table 12 is used to put an examiner's controller 27 and/or a patient's controller 28, and/or a tool used for optometry. The table 12 is supported by the base 11 to allow adjustment of the height (i.e., position in Y direction) of the table 12.

The column 13 is disposed at a rear side of the table 12 and is provided with an arm 14 at an upper part. The arm 14 is attached to the column 13 and supports a measurement headset 23 via a pair of driving mechanisms 22 above the table 12. The arm 14 is movable in Y direction with respect to the column 13. The arm 14 may further be configured to be movable in X and Z directions. The measurement unit 20 having the measurement headset 23 is provided at the end of the arm 14.

The base 11 is provided with a controller box 26b which accommodates a controller 26. The controller 26 integrally controls each part of the ophthalmologic apparatus 10. Power is supplied to the controller 26 from a commercial power source through a power cable 17a.

The measurement unit 20 is configured to operate at least one of subjective examinations and objective measurements. In the subjective examinations, the measurement unit 20 presents an eye chart to a patient and acquires measurement results based on a response from the patient against the presented eye chart. The subjective examinations include, for example, a visual field test as well as subjective refraction measurements such as far-sight examination, near-sight examination, contrast examination, and glare test. In the objective measurements, the measurement unit 20 illuminates light to an eye to be examined and detects reflected light to measure characteristics (i.e., acquire information) of the eye based on the detection results. The objective measurements include a process to measure characteristics of the eye to be examined and a process to capture an image of the eye. The objective measurements include, for example, an objective refractivity measurement, a corneal shape measurement, an intraocular pressure measurement, a fundus photographing, an optical coherence tomography (OCT), a tomographic photographing (also referred to as "OCT photographing"), and a measurement with OCT.

The measurement unit 20 is connected to the controller 26 via a control/power cable 17b and is supplied with power through the controller 26. The control/power cable 17b also establishes communication between the measurement unit 20 and the controller 26.

As illustrated in FIG. 2, the measurement unit 20 includes an attachment base 21, a left-eye driving mechanism 22L, a right-eye driving mechanism 22R, a left-eye measurement headset 23L supported by the left-eye driving mechanism 22L, and a right-eye measurement headset 23R supported by the right-eye driving mechanism 22R. The left-eye driving mechanism 22L and the right-eye driving mechanism 22R are attached to the attachment base 21.

The left-eye measurement headset 23L and the right-eye measurement headset 23R are configured to be symmetrical with respect to the vertical surface at the midpoint of them in X direction. The left-eye driving mechanism 22L and the right-eye driving mechanism 22R are also configured to be symmetrical with respect to the vertical surface at the midpoint of them in X direction. Unless otherwise stated, the following description regarding the measurement headset 23 and the driving mechanisms 22 is applicable to both sides thereof.

The attachment base 21 is fixed to the end of the arm 14 and is extended in X direction. The left-eye driving mechanism 22L is supported at one end of the attachment base 21 while the right-eye driving mechanism 22R is supported at the other end of the attachment base 21. The forehead rest 15 is supported at the center of the attachment base 21.

Upon receiving a control command from the controller 26, the left-eye driving mechanism 22L moves the position of the left-eye measurement headset 23L in X, Y, and Z directions as well as changes the direction of the left-eye measurement headset 23L with respect to an eye's swiveling axis OL of the left eye EL. As illustrated in FIG. 2, the left-eye driving mechanism 22L includes a left-vertical driver 22a, a left-horizontal driver 22b, and a left-swiveling driver 22c. The left-vertical driver 22a, the left-horizontal driver 22b, and the left-swiveling driver 22c are arranged between the attachment base 21 and the left-eye measurement headset 23L, in order from the upper side.

The left-vertical driver 22a moves the left-horizontal driver 22b in Y direction with respect to the attachment base 21. The left-horizontal driver 22b moves the left-swiveling driver 22c in X direction and Z direction with respect to the left-vertical driver 22a. The left-swiveling driver 22c swivels or rotates the left-eye measurement headset 23L about the eye's swiveling axis OL of the left eye EL with respect to the left-horizontal driver 22b.

Upon receiving a control command from the controller 26, the right-eye driving mechanism 22R moves the position of the right-eye measurement headset 23R in X, Y, and Z directions as well as changes the direction of the right-eye measurement headset 23R with respect to an eye's swiveling axis OL of the right eye ER. As illustrated in FIG. 2, the right-eye driving mechanism 22R includes a right-vertical driver 22*d*, a right-horizontal driver 22*e*, and a right-swiveling driver 22*f*. The right-vertical driver 22*d*, the right-horizontal driver 22*e*, and the right-swiveling driver 22*f* are arranged between the attachment base 21 and the right-eye measurement headset 23R, in order from the upper side.

The right-vertical driver 22*d* moves the right-horizontal driver 22*e* in Y direction with respect to the attachment base 21. The right-horizontal driver 22*e* moves the right-swiveling driver 22*f* in X direction and Z direction with respect to the right-vertical driver 22*d*. The right-swiveling driver 22*f* swivels or rotates the right-eye measurement headset 23R about the eye's swiveling axis OL of the right eye ER with respect to the right-horizontal driver 22*e*.

Each of the left-vertical driver 22*a*, the left-horizontal driver 22*b*, the right-vertical driver 22*d*, and the right-horizontal driver 22*e* includes an actuator for generating driving force and a transmission mechanism for transmitting the driving force. The actuator may be a pulse motor, and the transmission mechanism may include a plurality of gear sets and/or a plurality of rack and pinions. The left-horizontal driver 22*b* and the right-horizontal driver 22*e* may each include actuators and transmission mechanisms for the movements in X direction and Y direction, separately. This alternative configuration allows the structures of the drivers 22*b*, 22*e* simple, and therefore it becomes easy to control the horizontal movements of the drivers 22*b*, 22*e*.

Each of the left-swiveling driver 22*c* and the right-swiveling driver 22*f* also includes an actuator such as a pulse motor and a transmission mechanism including, for example, a plurality of gear sets and/or a plurality of rack and pinions. The left-swiveling driver 22*c* and the right-swiveling driver 22*f* each moves the corresponding transmission mechanism with the driving force generated by the actuator along a corresponding arc-shaped guide. Since the centers of the arc-shaped guides are the eye's swiveling axes OL, OR, the left-eye measurement headset 23L and the right-eye measurement headset 23R are swiveled or rotated about the eye's swiveling axis OL of the left eye EL and the eye's swiveling axis OL of the right eye ER, respectively.

It should be noted that each of the left-swiveling driver 22*c* and the right-swiveling driver 22*f* may be configured to have a rotation axis such that the left-eye measurement headset 23L and the right-eye measurement headset 23R are rotatable about the corresponding rotation axes.

By swiveling or rotating the left-eye measurement headset 23L and the right-eye measurement headset 23R to target directions using the left-swiveling driver 22*c* and the right-swiveling driver 22*f*, it is possible to move the eyes to be examined away from each other (i.e., divergence movements) and to move the eyes to be examined towards each other (i.e., convergence movements). With this, the ophthalmologic apparatus 10 is able to measure characteristics of the both eyes simultaneously by performing divergence movements and convergence movements and/or by performing far-sight examinations and near-sight examinations with both eyes.

As illustrated in FIGS. 2 and 3, the left-eye measurement headset 23L is equipped with a left-eye measurement optical system 24L and a left-eye deflection member 25L. The left-eye measurement optical system 24L is accommodated in a left housing 23*a* fixed to the left-swiveling driver 22*c*. The left-eye deflection member 25L is attached to an outer surface of the left housing 23*a*. The left-eye measurement headset 23L further includes, inside the left housing 23*a*, two cameras (stereo cameras) 40L, 41L near the left-eye deflection member 25L. The cameras 40L, 41L are arranged on both sides of the optical axis of the left-eye measurement optical system 24L in Z direction, and correspond to an imaging part. With the left-eye measurement headset 23L, light emitted from the left-eye measurement optical system 24L is deflected by the left-eye deflection member 25L and illuminates the left eye EL of the patient to measure the characteristics of the left eye. Each of the cameras 40L, 41L captures an image of the anterior ocular segment of the left eye EL (to be specific, an image of the anterior ocular segment captured from an obliquely-left or from an obliquely-right direction intersecting the visual axis of the left eye EL) through the left-eye deflection member 25L.

As illustrated in FIGS. 2 and 3, the right-eye measurement headset 23R is equipped with a right-eye measurement optical system 24R and a right-eye deflection member 25R. The right-eye measurement optical system 24R is accommodated in a right housing 23*b* fixed to the right-swiveling driver 22*f*. The right-eye deflection member 25R is attached to an outer surface of the right housing 23*b*. The right-eye measurement headset 23R further includes, inside the right housing 23*b*, two cameras (imaging part) 40R, 41R near the right-eye deflection member 25R. The cameras 40R, 41R are arranged on both sides of the optical axis of the right-eye measurement optical system 24R in Z direction. With the right-eye measurement headset 23R, light emitted from the right-eye measurement optical system 24R is deflected by the right-eye deflection member 25R and illuminates the right eye ER of the patient to measure the characteristics of the right eye. Each of the cameras 40R, 41R captures an image of the anterior ocular segment of the right eye ER through the right-eye deflection member 25R.

In the embodiment of the disclosure, each of the cameras 40, 41 captures the eyes to be examined E (i.e., EL and ER) from different directions substantially simultaneously so as to acquire two different anterior ocular segment images. It should be noted that the cameras 40L, 41L and the cameras 40R, 41R may be arranged on both sides of the corresponding optical axes in Y direction. Further, the number of cameras for each eye should not be limited to two. Each of the left-eye measurement headset 23L and the right-eye measurement headset 23R may be equipped with three or more cameras and captures more images of the anterior ocular segment. Additionally, the installation positions of the cameras 40, 41 may be modified in accordance with, for example, a size of each component and/or design of the measurement headsets 23L, 23R.

In the disclosure, the meaning of "substantially simultaneous(ly)" includes a deviation in image-capturing timing of the cameras 40, 41 to the extent that eye movement can be ignored. With two or more of cameras 40, 41, the anterior ocular segment of the eye to be examined E is captured from different directions substantially simultaneously. That is, the ophthalmologic apparatus 10 of the embodiment is able to acquire two or more images of the eye E while the eye E is oriented in one direction.

The left-eye measurement optical system 24L and the right-eye measurement optical system 24R each includes, for example, a visual acuity testing device, a phoropter, a refraction meter or a wavefront sensor for measuring refractive power, an eye fundus camera for capturing an eye fundus image, a tomography photographing device for capturing a retina tomographic image, a specular microscope for capturing a corneal endothelium image, a keratometer for measuring a corneal shape, or a tonometer for measuring intraocular pressure, or any combinations thereof. Here, the visual acuity testing device is used to operate an acuity test while switching eye charts. The phoropter is used to determine an accurate correction value of the eye to be examined by switching correction lenses.

Figure 5:
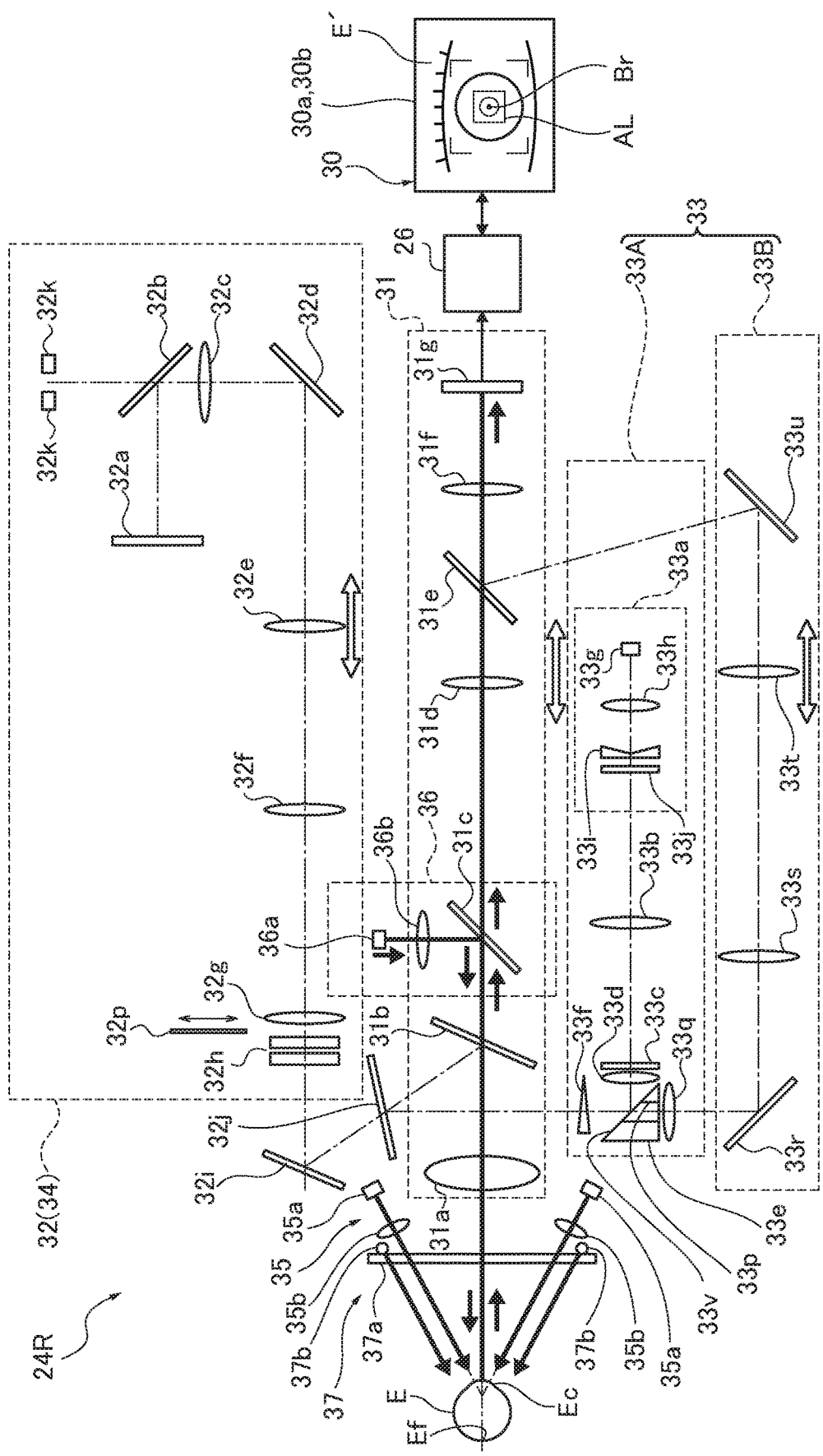
FIG. 5 is an explanatory view illustrating a right eye measurement optical system of the ophthalmologic apparatus according to the embodiment.

An example of the left-eye measurement optical system 24L and the right-eye measurement optical system 24R will be described with reference to FIGS. 3 and 5. FIG. 3 illustrates a schematic configuration of the left-eye measurement optical system 24L and the right-eye measurement optical system 24R of the ophthalmologic apparatus 10 according to the embodiment. FIG. 5 illustrates a detailed configuration of the right-eye measurement optical system 24R. The left-eye measurement optical system 24L is omitted in FIG. 5. Since the configuration of the left-eye measurement optical system 24L is identical to that of the configuration of the right-eye measurement optical system 24R, the following description is made only for the right-eye measurement optical system 24R.

As illustrated in FIG. 5, the right-eye measurement optical system 24R includes an observation system 31, a target projection system 32, an ocular-refractive-power measurement system 33, a subjective examination system 34, an alignment optical system 35, an alignment optical system 36, and a kerato system 37. The observation system 31 observes or monitors an anterior ocular segment of the eye to be examined E. The target projection system 32 projects a target onto the eye to be examined E. The ocular-refractive-power measurement system measures ocular refractive power of the eye E. The subjective examination system 34 carries out a subjective examination on the eye E.

The ocular-refractive-power measurement system 33 of the embodiment has function of projecting a predetermined measuring pattern onto the ocular fundus Ef of the eye to be examined E and function of detecting an image having the predetermined measuring pattern projected onto the ocular fundus Ef. Accordingly, the ocular-refractive-power measurement system 33 functions as a first measurement system in which a light flux is projected onto the ocular fundus Ef of the eye to be examined E and the reflection light from the ocular fundus Ef is received.

The subjective examination system 34 of the embodiment has function of projecting the target onto the eye to be examined E and shares optical elements of the optical system with the target projection system 32. The alignment optical systems 35, 36 carry out positioning or alignment of the optical system with respect to the eye to be examined E. The controller 26 uses the alignment optical system 35 to acquire alignment information in Z direction, which is along the optical axis of the observation system 31. The controller 26 further uses the alignment optical system 36 to acquire alignment information in Y direction and X direction, which are perpendicular to the optical axis of the system.

The observation system 31 includes an objective lens 31a, a dichroic filter 31b, a half mirror 31c, a relay lens 31d, a dichroic filter 31e, an imaging lens 31f, and an image pickup element (e.g., CCD) 31g. In the observation system 31, the light flux reflected by the eye to be examined E (specifically, anterior ocular segment) passes through the objective lens 31a and is imaged on the image pickup element 31g by the imaging lens 31f. Accordingly, the image pickup element 31g forms an image of the anterior ocular segment E onto which a kerato-ring light flux and/or a light flux of an alignment light source 35a and/or a light flux of an alignment light source 36a are projected. The controller 26 displays, for example, an image of the anterior ocular segment E, which is formed based on image signals outputted from the image pickup element 31g, on a display surface 30a of a display 30. The kerato system 37 is provided in front of the objective lens 31a.

The kerato system 37 includes a kerato board 37a and a kerato-ring light source 37b. The kerato board 37a is a board having a slit concentric with the optical axis of the observation system 31 and is provided in the vicinity of the objective lens 31a. The kerato-ring light source 37b is provided along with the slit of the kerato board 37a. In the kerato system 37, the light flux from the kerato-ring light source 37b passes through the slit of the kerato board 37a so as to project a kerato-ring light flux for corneal shape measurement (i.e., ring-shaped target for corneal curvature measurement) onto the eye to be examined E (specifically, cornea Ec thereof). The kerato-ring light flux is reflected by the cornea Ec of the eye to be examined E and is imaged on the image pickup element 31g by the observation system 31. That is, the pickup element 31g detects or receives an image of the kerato-ring light flux, and the controller 26 displays an image having the measuring pattern on the display surface 30a. Additionally, the controller 26 measures a corneal shape (i.e., curvature radius) of the eye using a known method based on the image signal sent from the image pickup element 31g. Accordingly, the kerato system 37 functions as a second measurement system in which a light flux is projected onto the anterior ocular segment (i.e., cornea Ec) of the eye to be examined E and the characteristics of the anterior ocular segment (i.e., cornea Ec) is measured based on the reflection light from the anterior ocular segment (i.e., cornea Ec). That is, the kerato system 37 functions as a corneal shape measurement system for measuring a corneal shape of the eye to be examined E. In this embodiment, the kerato system 37 includes the kerato board 37a which has about one to three ring-slits and used to measure a curvature around the center of the cornea. However, the configuration of the kerato system 37 is not limited thereto. So long as the kerato system 37 is capable of measuring a corneal shape, a placido board, which has multiple rings and allows measuring an entire corneal shape, may be used in the embodiment. The alignment optical system 35 is provided behind the kerato system (i.e., kerato board 37a).

The alignment optical system 35 includes a pair of alignment light sources 35a and a pair of projection lenses 35b. The light flux from each of the alignment light sources 35a is converted to a parallel luminous flux by the corresponding projection lens 35b. The parallel luminous light flux then passes through the alignment slit of the kerato board 37 and is projected onto the cornea Ec of the eye to be examined E. Accordingly, an alignment optical target is projected onto the cornea of the eye to be examined E. This optical target is detected as a virtual image (Purkinje image) formed by the reflection on the corneal surface. The alignment with the optical target at least includes the alignment in the optical axis of the measurement optical system 24R. Additionally, the alignment with the optical target may include the alignment in X direction and Y direction.

In the embodiment, the optical axis of the measurement optical system 24R is deflected by the right-eye deflection member 25R, and the optical axis of the measurement optical system 24R substantially coincides with Z direction at the position of a mirror image of the measurement optical system 24R with respect to the right-eye deflection member 25R. That is, the alignment in the optical axis of the measurement optical system 24R corresponds to the alignment in Z direction.

The alignment information in Z direction (i.e., moving amount in Z direction) is acquired by analyzing two or more of the images captured by the two cameras 40, 41 substantially simultaneously. The alignment information in X and Y directions (i.e., moving amounts in X and Y directions) is acquired or calculated based on a bright spot (i.e., bright spot image Br) which is projected onto the cornea Ex on the anterior ocular segment image obtained by the image pickup element 31g.

The controller 26 drives the right-horizontal driver 22e in accordance with the acquired alignment information to move the right-eye measurement headset 23R in Z direction. Accordingly, the alignment or positioning of the right-eye measurement headset 23R in Z direction, which coincides with the optical axis of the observation system 31, is performed. With the alignment or positioning of the right-eye measurement headset 23R, a ratio of a diameter of the kerato-ring image and a distance between the two bright spot images Br on the image pickup element 31g, which are formed by the light from the alignment light sources 35a, becomes within a predetermined range.

It should be noted that the controller 26 may be configured to calculate a shift amount of the alignment based on the ratio and to display the calculated shift amount on the display surface 30a. Further, the alignment in Z direction may alternatively be performed by adjusting the position of the right-eye measurement headset 23R to focus bright spots Br formed by the alignment light source 36a. Here, the "shift amount" in this disclosure means a displacement or a gap of the actual alignment from the desired alignment.

The observation system 31 is equipped with the alignment optical system 36. The alignment optical system 36 includes the alignment light source 36a and a projection lens 36b and shares the half mirror 31c, the dichroic filter 31b, and the objective lens 31a with the observation system 31. In the alignment optical system 36, a light flux from the alignment light source 36a is converted into a parallel luminous flux by the objective lens 31a, and the parallel luminous flux is projected onto the cornea Ec. The controller 26 acquires alignment information (e.g., shift amounts in Y and X directions) based on a bright spot (i.e., bright spot image) projected onto the cornea Ec of the anterior ocular segment image E' of the eye to be examined E. The controller 26 drives the right-horizontal driver 22e and the right-vertical driver 22d in accordance with the acquired alignment information to move the right-eye measurement headset 23R in X direction and Y direction. Accordingly, the alignment or positioning of the right-eye measurement headset 23R in X direction and in Y direction is performed. In addition to the anterior ocular segment image E' with the bright spot image Br, the controller 26 displays an alignment mark AL for alignment on the display surface 30a. Additionally, the controller 26 may be configured to commence the measurement once the alignment is completed.

The target projection system 32 (i.e., subjective examination system 34) includes a display 32a, a half mirror 32b, a relay lens 32c, a reflection mirror 32d, a focusing lens 32e, a relay lens 32f, a field lens 32g, a variable cross cylinder (VCC) lens 32h, a reflection les 32i, and a dichroic filter 32j. Additionally, the target projection system 32 shares the dichroic filter 31b and the objective lens 31a with the observation system 31.

The subjective examination system 34 further includes at least two glare light sources 32k to surround an optical axis in a different optical path from the optical path for the display 32a and the like. The glare light sources 32k emits glare light to the eye to be examined E. The display 32a presents a fixation target and/or a dot-shaped target to fix the eye to be examined E and a subjective examination target to examine the characteristics of the eye to be examined E subjectively. Such characteristics include a visual acuity value and a correction degree (i.e., far-sight diopter and near-sight diopter), for example. The display 32a may be an Electroluminescence (EL) or a Liquid Crystal Display (LCD), and displays an image in accordance with the control of the controller 26. The display 32a is provided movable along the optical axis in the optical path of the target projection system 32 and the subjective examination system 34 so as to be arranged at a position optically conjugated with the fundus Ef of the eye to be examined E.

The target projection system 32 and the subjective examination system 34 further include a pinhole plate 32p in the optical path at a position substantially conjugated with the pupil of the eye to be examined E. The pinhole plate 32p has a through-hole and is provided insertable to and removable from the optical path connected with the target projection system 32 (and subjective examination system 34). When the pinhole plate 32p is inserted to the optical path, the through-hole is positioned on the optical axis. By inserting the pinhole plate 32p to the optical path in the subjective examination mode, the ophthalmologic apparatus 10 of this embodiment is able to conduct a pinhole test. The pinhole test allows determining the availability of correction on the eye to be examined E with glasses. The pinhole plate 32p of the embodiment is provided between the field lens 32g and the VCC 32h and is inserted thereto and removed therefrom under the control of the controller 26. Here, the position of the pinhole plate 32p is only an example. So long as the pinhole is provided at a position on the optical path substantially conjugated with the pupil of the eye to be examined E, the position is not limited thereto.

The ocular-refractive-power measurement system 33 includes a ring-shaped light flux projection system 33A and a ring-shaped light flux receiving system 33B. The ring-shaped light flux projection system 33A projects a ring-shaped measurement pattern on the fundus Ef of the eye to be examined E. The ring-shaped light flux receiving system 33B detects or receives reflection light of the ring-shaped measurement pattern reflected from the fundus Ef. The ring-shaped light flux projection system 33A includes a refraction light source unit 33a, a relay lens 33b, a pupil ring diaphragm 33c, a field lens 33d, a holed prism 33e, and a rotary prism 33f. Additionally, the ring-shaped light flux projection system 33A shares the dichroic filter 32j with the target projection system 32 (i.e., subjective examination system 34), as well as shares the dichroic filter 31b and the objective lens 31a with the observation system 31. The refraction light source unit 33a may include a refraction measuring light source 33g for refraction measurement with an LED or the like, a collimator lens 33h, a conical lens 33i, and a ring-pattern forming plate 33j. The refraction measuring light source 33g, the collimator lens 33h, the conical lens 33i, and the ring-pattern forming plate 33j are integrally movable in the optical axis of the ocular-refractive-power measurement system 33 under the control of the controller 26.

The ring-shaped light flux receiving system 33B includes a hole 33p of the holed prism 33e, a field lens 33q, a reflection mirror 33r, a relay lens 33s, a focusing lens 33t, and a reflection mirror 33u. Additionally, the ring-shaped light flux receiving system 33B shares the objective lens 31a, the dichroic filter 31b, the dichroic filter 31e, the imaging lens 31f, and the image pickup element 31g with the observation system 31, shares the dichroic filter 32j with the target projection system 32 (i.e., subjective examination system 34), and shares the rotary prism 33f and the holed prism 33e with the ring-shaped light flux projection system 33A.

The measurement process and the subjective examination method with this type of the right-eye measurement optical system 24R and the left-eye measurement optical system 24L may be conducted in the same manner as that of JP2017-63978A.

Figure 6:
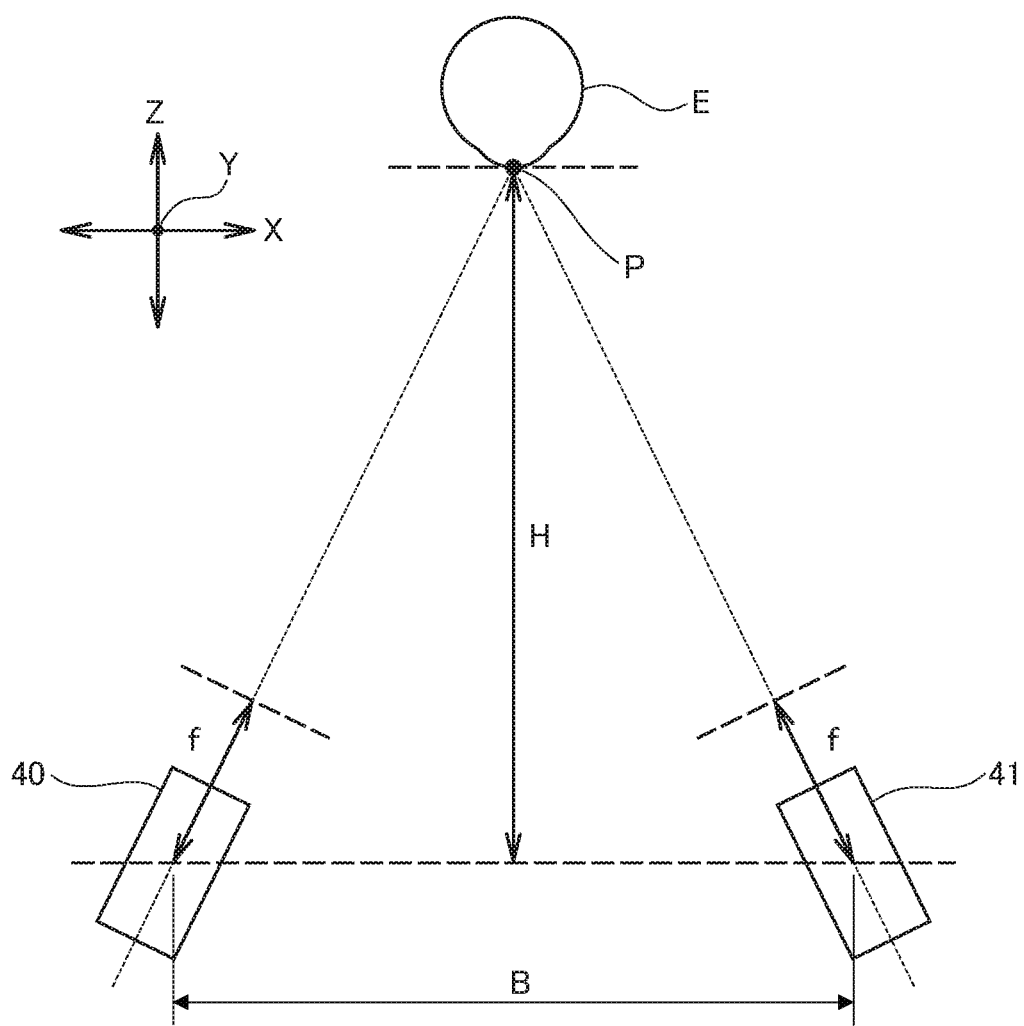
FIG. 6 is a schematic view illustrating a positional relationship between an eye to be examined and two cameras provided to the ophthalmologic apparatus of the embodiment.

The controller 26 integrally controls each part of the ophthalmologic apparatus 10. As illustrated in FIG. 6, the controller 26 is connected with the left-eye measurement optical system 24L, the right-eye measurement optical system 24R, the drivers 22a, 22b, 22c of the left-eye driving mechanism 22L, the drivers 22d, 22e, 22f of the right-eye driving mechanism 22R, and an arm driving mechanism 16. Additionally, the cameras 40L, 41L, the cameras 40R, 41R, the examiner's controller (first inputter) 27 and the patient's controller (second inputter) 28, and a storage 29 are connected with the controller 26.

The examiner controls the examiner's controller 27 to manipulate the ophthalmologic apparatus 10. The examiner's controller 27 and the controller 26 are communicably connected to each other by short-range wireless communication or by wired communication.

The examiner's controller 27 of the embodiment is a mobile terminal (i.e., data processing device) such as a tablet or a smartphone. The examiner is thus able to hold the controller 27 with his/her hand and manipulates the controller from any position with respect to the patient and/or to the ophthalmologic apparatus 10, resulting in improving flexibility of the examiner during the measurement. It should be noted that the examiner's controller 27 may also be placed on the table 12. Needless to say, the examiner's controller 27 is not limited to a mobile terminal, but may be a laptop computer or a desktop computer.

Figure 4:
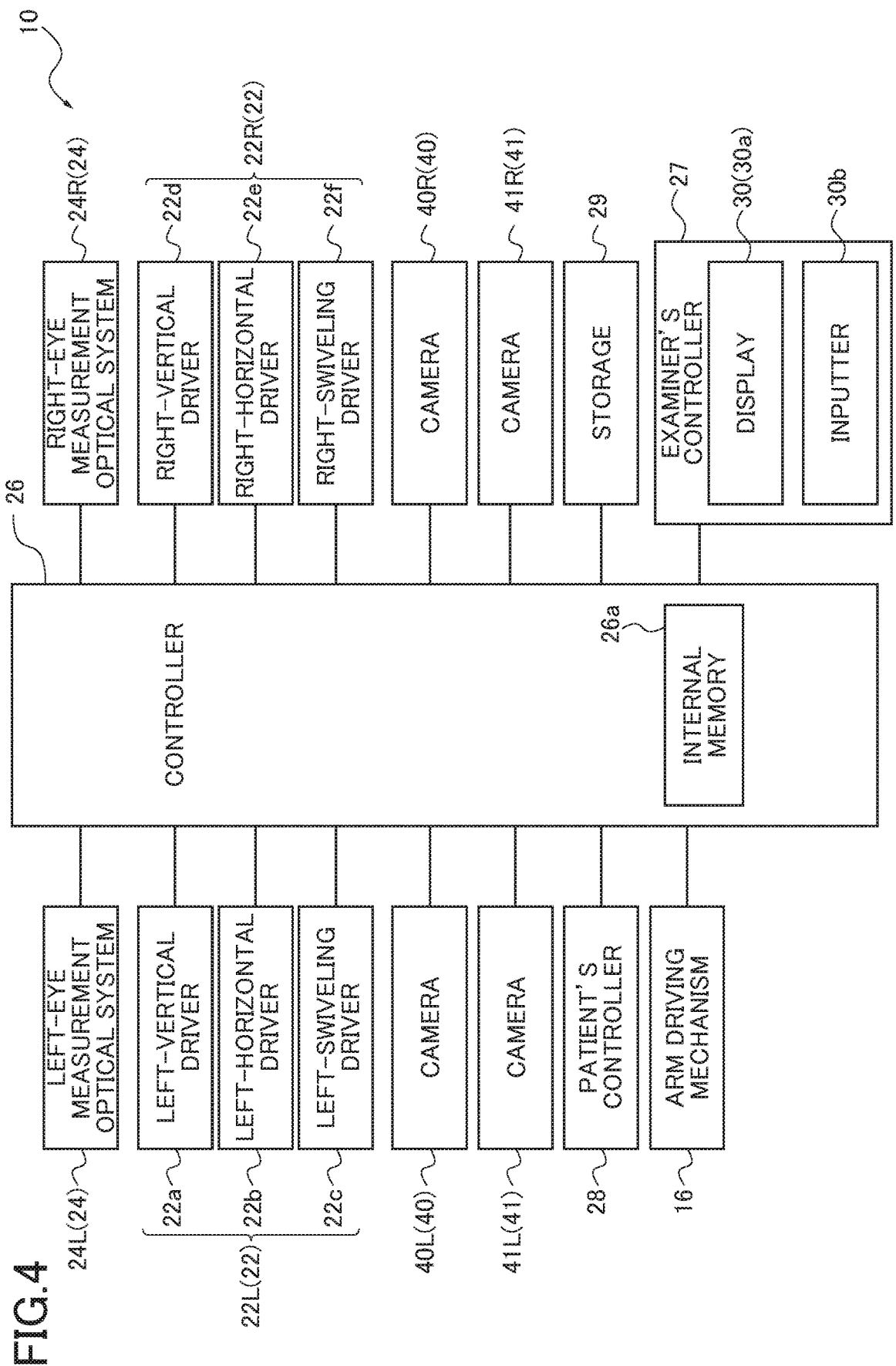
FIG. 4 is a block diagram illustrating a control system of the ophthalmologic apparatus according to the embodiment.
Figure 7:
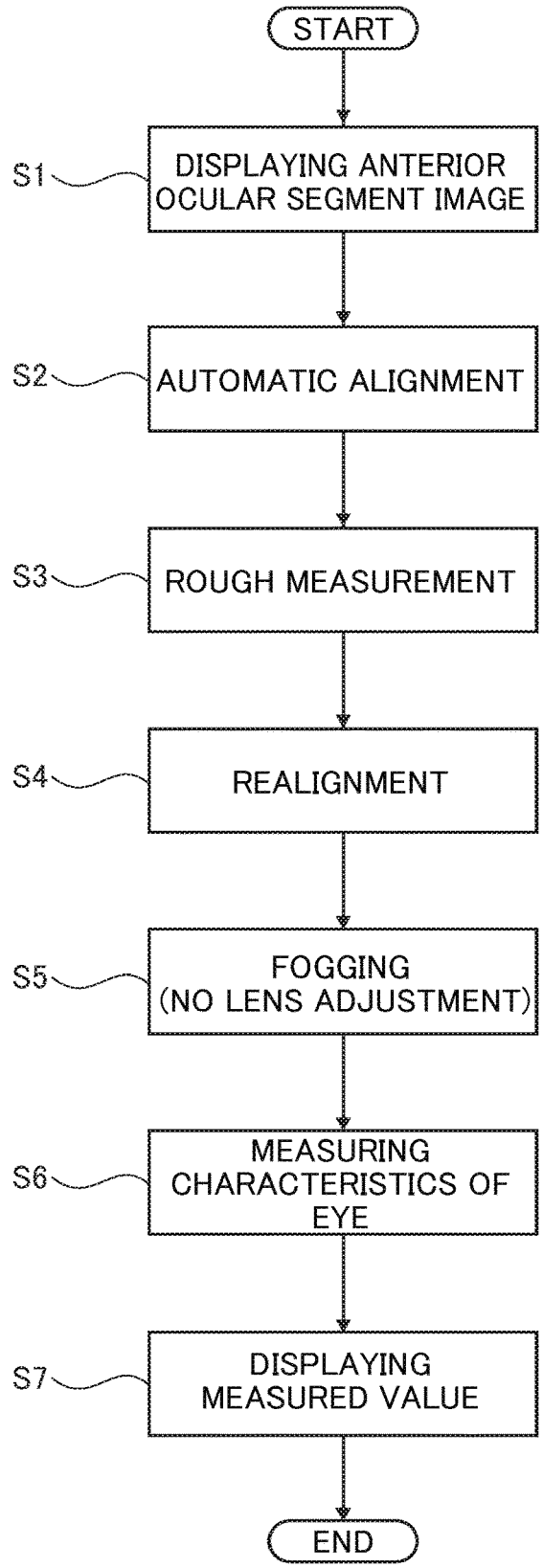
FIG. 7 is a flowchart showing an example of operation carried out by the ophthalmologic apparatus of the embodiment.

The examiner's controller 27 is equipped with the display 30 made of a liquid crystal monitor. The display 30 includes a touch-panel inputter 30b superimposingly arranged on the display surface 30a, as illustrated in FIGS. 4 and 7. When measuring the characteristics of the eye to be examined E, the examiner inputs a command for the alignment and a command for the measurement through the inputter 30b. The display surface 30a displays the anterior ocular segment image E, which is generated based on image signals outputted from the image pickup element (i.e., CCD) 31g of the observation system 31, on an operation screen 50 (see FIG. 8) which functions as the inputter 30b, and the like.

The patient controls the patient's controller 28 to make a response during each measurement on the eye to be examined E. The patient's controller 28 is equipped with an inputting device such as a keyboard, a mouse, a joystick, and the like. The patient's controller 28 is connected with the controller 26 by short-range wireless communication or by wired communication.

The controller 26 develops the program stored in the storage 29 or in an internal memory 26a to, for example, a RAM, and integrally controls the ophthalmologic apparatus 10 in accordance with the operation inputted to the examiner's controller 27 and/or to the patient's controller 28. In the embodiment, the internal memory 26a is configured with, for example, a RAM, and the storage 29 is configured with, for example, a ROM and/or an EEPROM.

An example of the alignment in X, Y, and Z directions of the measurement headsets 23 and an example of the measurement of the ocular refractive power with the aforementioned ophthalmologic apparatus 10 of the embodiment will be described with reference to the flowchart of FIG. 7 and the screens illustrated in FIGS. 8-11.

The ophthalmologic apparatus 10 of the embodiment is configured to perform, under the control of the controller 26, the analysis on the two anterior ocular segment images of the eye to be examined E, which are captured by the two cameras 40, 41, and the automatic alignment of the measurement headsets 23 by controlling the driving mechanisms 22 in accordance with the analysis results. Additionally, the ophthalmologic apparatus 10 is configured to allow the examiner to confirm the alignment and the condition of the eye to be examined E with the anterior ocular segment image E (i.e., front view of the eye) displayed on the display 30 of the examiner's controller 27. With this, it is possible to promptly and accurately carry out the alignment and to promptly and accurately measure the characteristics of the eye to be examined E.

As is known, it may be difficult to carry out the alignment with undesirable conditions of the eye to be examined E. Such conditions may occur due to, for example, a failure of the fixation of the eye E, a failure of binocular vision, heterophoria, blepharoptosis, suppression of the eye E, mosis (i.e., constriction of the pupil), head tilt, or the like. However, it is difficult to specify a cause of misalignment since conventional images displayed on a display for alignment are images captured by two or more of cameras from oblique directions with respect to the anterior ocular segment of the eye to be examined E or a composite image of those images.

In contrast, the ophthalmologic apparatus 10 of the embodiment allows the examiner to visually confirm the anterior ocular segment image E (i.e., front view) of the eye to be examined E on the operation screen 50 during the alignment. Thus, the examiner is able to precisely specify a cause of misalignment and to eliminate the cause by, for example, correcting the position of the head and/or by giving an instruction to the patient. As a result, the accuracy and success rate of the alignment improves.

In order to measure the characteristics of the eye to be examined E, the ophthalmologic apparatus 10 is powered ON. A browser or an application in the examiner's controller 27 is then started to display the operation screen 50 for the ophthalmologic apparatus 10 on the display surface 30a (see FIG. 8).

Figure 8:
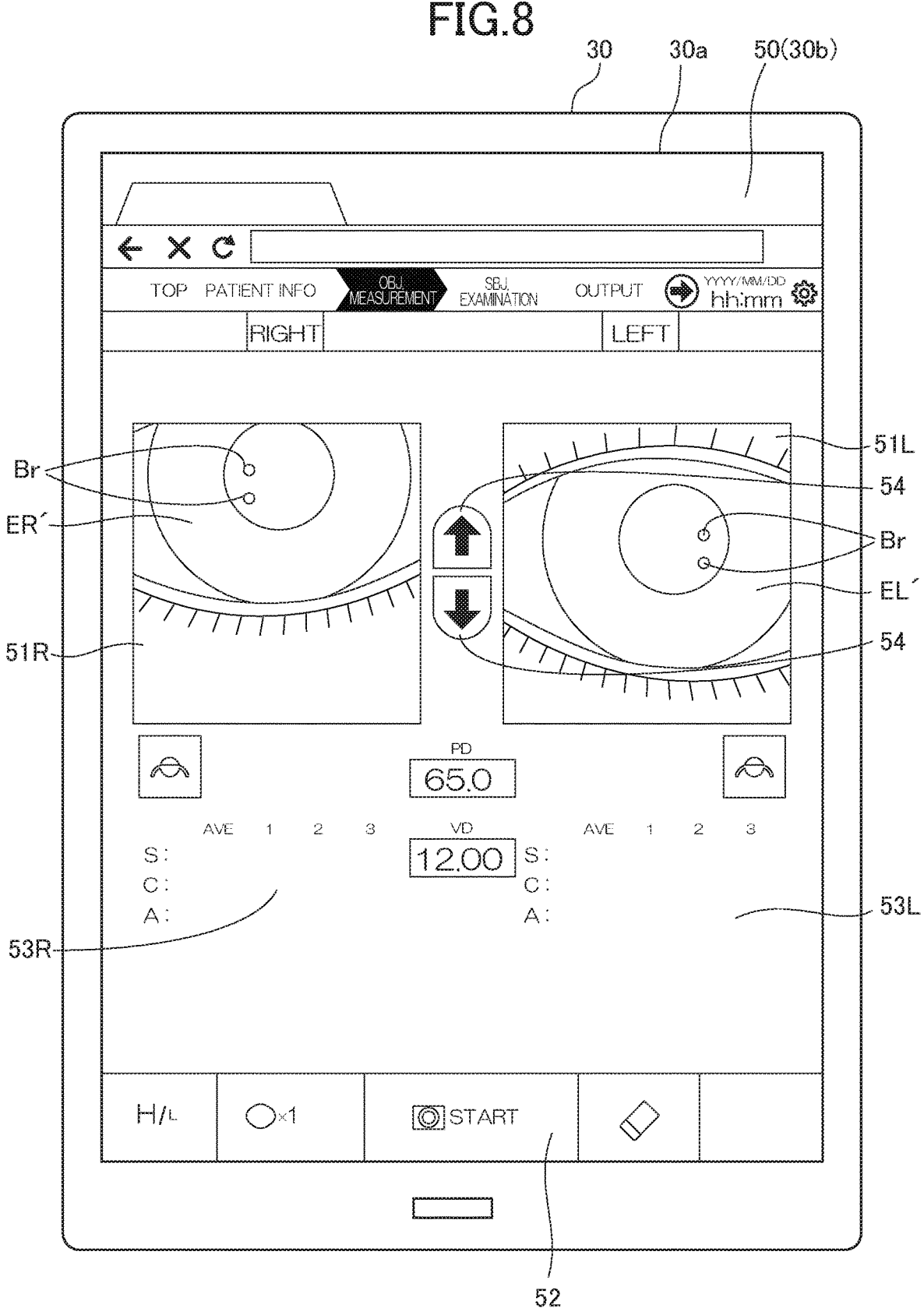
FIG. 8 is a view illustrating an example of image displayed on a display of the ophthalmologic apparatus of the embodiment.

The patient sits on a chair in front of the ophthalmologic apparatus 10 and puts his/her head on the forehead rest 15. The ophthalmologic apparatus 10 then starts capturing images of the anterior ocular segments of the left eye EL and the right eye ER with the observation systems 31 of the measurement optical systems 24. As illustrated in FIG. 8, the controller 26 displays the anterior ocular segment images (front views) EL', ER' of the left eye EL and the right eye ER, which are generated from image signals outputted from the image pickup elements 31g, in anterior ocular segment display areas 51L, 51R of the operation screen 50.

The anterior ocular segment images EL', ER' may be generated and displayed when the ophthalmologic apparatus 10 is powered ON or when a sensor detects that the patient puts his/her head on the forehead rest 15. Alternatively, the images EL', ER' may be generated and displayed when the examiner sends a command to the ophthalmologic apparatus 10 through the operation screen 50.

When the position of the anterior ocular segment image EL', ER' is considerably deviated from the center of the anterior ocular segment display area 51L, 51R, the examiner manipulates an up-and-down button 54 on the operation screen 50. The arm is vertically moved in accordance with the operation of the button 54. With this, a rough adjustment for the height of the measurement headsets 23 with respect to the eye to be examined E is realized.

After the rough adjustment for the height, the automatic alignment (i.e., automatic positioning) is performed (in Step S2). FIG. 8 illustrates an anterior ocular segment image ER' of the right-eye ER before the automatic alignment. The upper part of the anterior ocular segment image ER' is not displayed in the area 51R. That is, the position of the right-eye ER is deviated from an appropriate position. If the deviation is caused by head tilt of the patient, the examiner can promptly instruct and/or support the patient to correct the position of his/her head to an appropriate position.

The process for the automatic alignment at Step S2 is described in detail. The ophthalmologic apparatus 10 starts the automatic alignment process when the examiner touches a measurement start button 52 on the operation screen 50. By receiving the start command, the controller 26 controls the alignment optical system 35 and projects the parallel luminous flux to the cornea Ec of the eye to be examined E through the alignment slit of the kerato board 37. Accordingly, the optical target for the alignment is projected onto the cornea of the eye. This optical target is detected as a virtual image (Purkinje image) formed by the reflection from the corneal surface.

The controller 26 then acquires alignment information in XY directions (i.e., moving amounts in X and Y directions) based on the bright spot image Br formed in the anterior ocular segment image E'.

Additionally, the controller 26 controls the cameras 40, 41 to capture or film images of the anterior ocular segment of the eye E from two different directions substantially simultaneously. This filming is carried out as moving image photographing. Each of the cameras 40, 41 films the eye E at a predetermined frame rate and sequentially sends the captured frames to the controller 26 in real-time. The controller 26 associates the frames received from each of the cameras 40, 41 in accordance with the image-capturing timing.

The controller 26 corrects distortion of each frame based on aberration information stored in the storage 29. This correction process may be carried out in accordance with a known image processing method such as a method for correcting distortion aberration with correction coefficients.

The controller 26 analyzes each of the distortion-corrected frames to identify a feature position. An example of such a feature position may be a position in the image corresponding to the pupil center of the anterior ocular segment. To be specific, the controller 26 identifies an image area (i.e., pupil area) corresponding to the pupil of the eye E based on distribution of pixel values (e.g., brightness values) of the filmed image (i.e., image of anterior ocular segment). As pupils are generally captured and imaged with lower brightness than other parts of the eye, it allows the controller 26 to identify the pupil area by searching am image area having low brightness values. Additionally, the controller 26 may identify the pupil area with the shape of the pupil in mind. That is, the controller 26 may be configured to identify the pupil area by searching an image area having a substantially circular shape and low brightness values so as to improve the accuracy.

The controller 26 then identifies a center position of the pupil area. As the pupil has a substantially circular shape, the outline of the pupil area is an approximate circle or an approximate ellipse. Accordingly, the controller 26 determines the center position by identifying the outline of the pupil area and defines the determined center position as the pupil center. Alternatively, the controller 26 may determine the gravity center of the pupil area and define the gravity center as the pupil center.

It should be noted that the controller 26 may determine a feature position corresponding to another feature point of the eye E based on distribution of pixel values of the filmed image, as described above.

Following steps to acquire three-dimensional position information of the eye to be examined E based on the determined feature position (i.e., pupil center) will be described with reference to FIG. 6. FIG. 6 is a schematic view illustrating a positional relationship between the eye E and the two cameras 40, 41.

In FIG. 6, a distance (i.e., baseline length) between the two cameras 40, 41 is denoted by "B". A distance (i.e., photographing distance) from the baseline of the two cameras 40, 41 to the feature point P of the eye E is denoted by "H". A distance (i.e., screen distance) between each of the cameras 40, 41 and the corresponding screen surface is denoted by "f".

Under the arrangement, the resolutions of the filmed image obtained by the cameras 40, 41 are calculated by the following equations:

Resolution in XY direction (two-dimensional resolution): $\Delta_{XY} = H \times \Delta_p / f$ Resolution in Z direction (depth resolution): $\Delta_Z = H \times H \times \Delta_p / (B \times f)$ where $\Delta_p$ represents a pixel resolution.

By applying a known trigonometry, the controller 26 calculates the three-dimensional position of the feature point P (i.e., three-dimensional position of eye E) based on the positions of the two cameras 40, 41 and feature positions in the two of the captured images. Here, the feature positions in the images represent the feature point P of the eye E.

The controller 26 obtains alignment information in Z direction based on the calculated three-dimensional position of the eye E. The alignment information in Z direction is to align the optical axis of the measurement optical system 24 with the axis of the eye E and to move the measurement optical system 24 to a position away from the eye E by a predetermined operating distance by controlling the driving mechanism 22. The "operating distance" in this disclosure means a distance between the eye E and the measurement optical system 24 when the measurement optical system 24 measures the optical features of the eye E. The operating distance may also be called a working distance and is a predetermined value.

Based upon the obtained alignment information, the controller 26 drives the driving mechanism 22 to move the measurement headsets 23 in X, Y, and Z directions to carry out the alignment in X, Y, and Z directions. The alignment is independently performed for each of the left-eye measurement headset 23L and the right-eye measurement headset 23R. Although a left eye EL and a right eye ER of a patient may not be positioned symmetrically, the controller 26 is, therefore, able to align the measurement headsets 23 accurately in accordance with the positions of left eye EL and right eye ER.

In order to film the anterior ocular segment from different directions with the cameras 40, 41, the controller 26 may implement the following processes (1) and (2) to move the measurement optical system 24 along with movements of the eye to be examined E. Accordingly, the alignment of the measurement headsets 23 and the measurement of the characteristics of the eye E is appropriately achieved.

(1) The controller 26 successively analyzes two or more of frames of video images, which are captured by the cameras 40, 41 substantially simultaneously, and successively determines the three-dimensional position of the eye to be examined E. (2) The controller 26 successively controls the driving mechanism 22 based on the successively-determined three-dimensional position of the eye E. Accordingly, the controller 26 moves the measurement optical system 24 along with the movements of the eye E.

Figure 9:
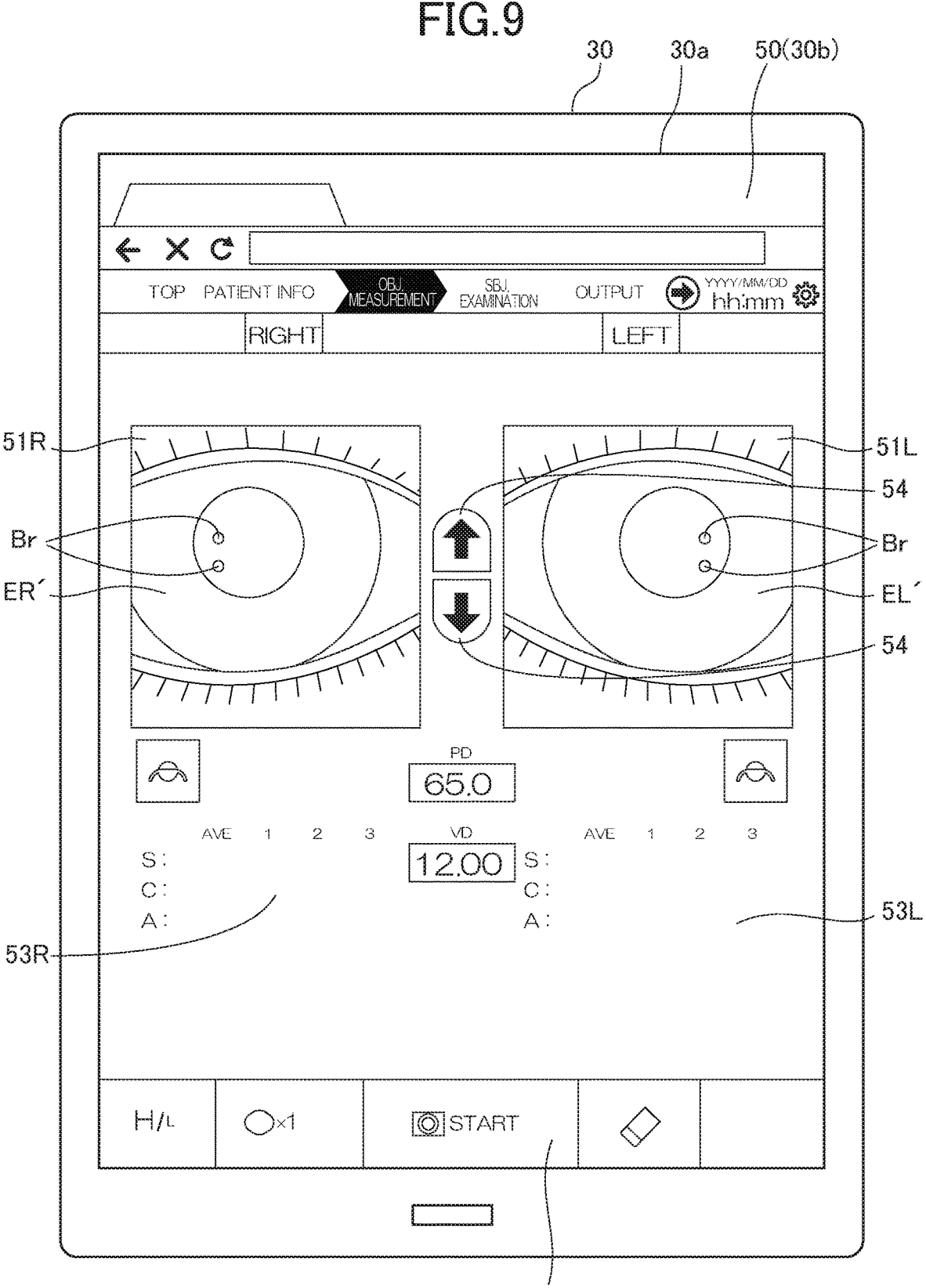
FIG. 9 is a view illustrating another example of image displayed on the display of the ophthalmologic apparatus of the embodiment.

FIG. 9 is a view illustrating an image displayed on the screen 50, in which both of the right and left anterior ocular segment images EL', ER' are displayed at appropriate positions in the anterior ocular segment display areas 51L, 51R. By continuously displaying the anterior ocular segment images EL', ER' on the operation screen 50 in real-time, it allows the examiner to determine whether the alignment is appropriately achieved while operating the apparatus to prepare for measurement.

After completing the alignment, the program proceeds to Step S3, in which a rough measurement of ocular refractive power is carried out as a provisional measurement. The "rough measurement" in this disclosure means a preliminary measurement for understanding a rough ocular refractive power of the eye E and for determining a moving amount of the focusing lens 32e prior to a non-provisional measurement. Specifically, the focusing lens 32e is first arranged at a position for 0 [D (diopter)]. The eye to be examined E is then fixed on the fixation target, and the rough measurement is carried out by the ocular-refractive-power measurement system 33.

The program proceeds to Step S4, in which realignment is carried out for the non-provisional measurement. The realignment is realized in the same manner as the auto-alignment in Step S2.

The program proceeds to Step S5, in which the focusing lens 32e is moved to a position out of focus to have the eye E in a fogging state. With the fogging state, the patient having weak astigmatism sees a blurred image in a longitude direction. That is, the eye to be examined E is brought to an adjustment-pausing state (i.e., adjustment-removal state for lens of eye E). The non-provisional measurement of ocular refractive power is carried out under the adjustment-pausing state in Step S6.

Figure 10:
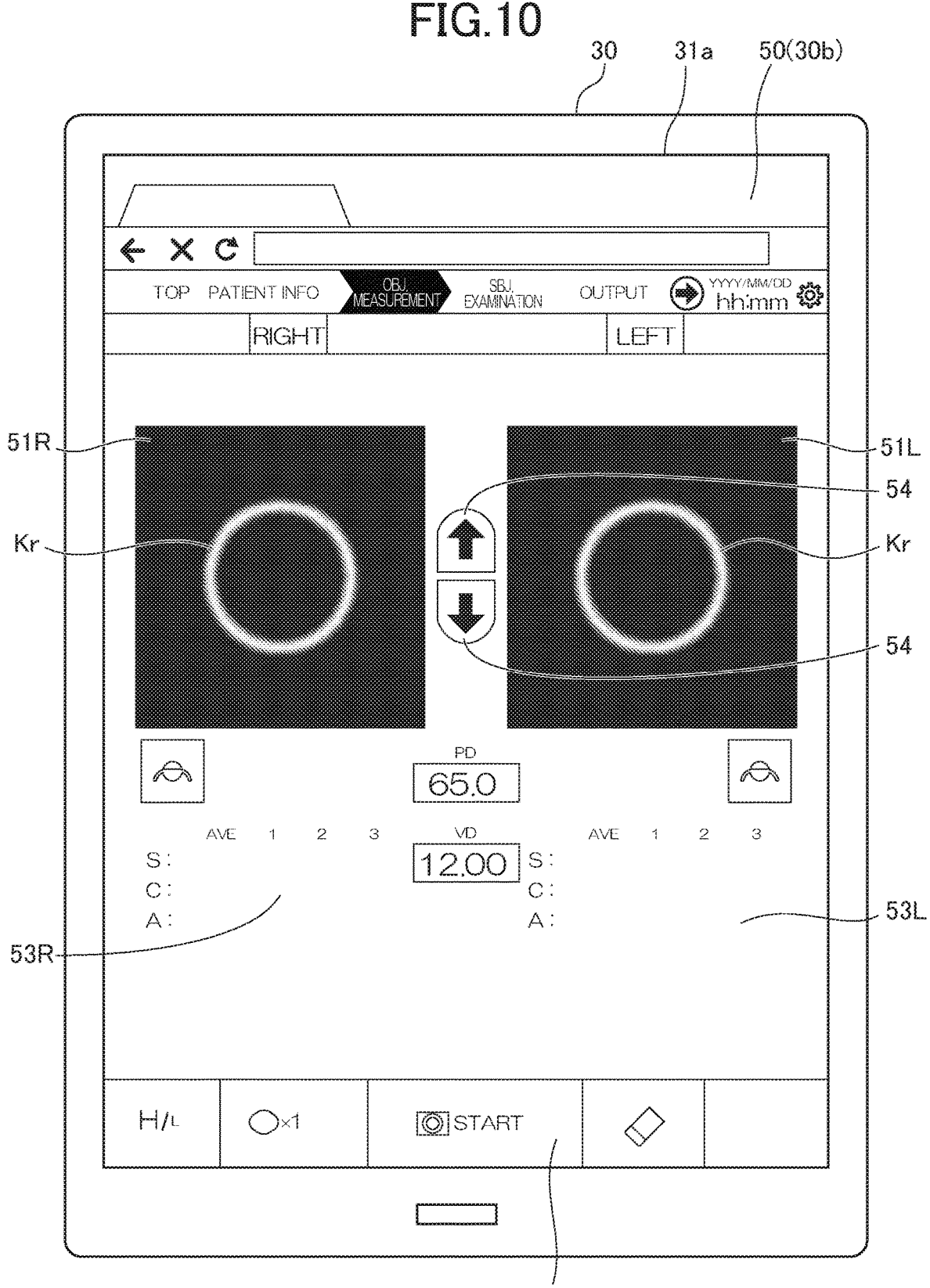
FIG. 10 is a view illustrating another example of image displayed on the display of the ophthalmologic apparatus of the embodiment.

In Step S6, the non-provisional measurement (i.e., refraction measurement) of the eye to be examined E is carried out. To be specific, the controller 26 drives the ocular-refractive-power measurement system 33 based on spherical power S, cylindrical power C, and axis angle (cylinder axis angle) Ax obtained by the rough measurement. FIG. 10 shows the operation screen 50 during the refraction measurement. As shown, a measuring pattern image Kr having a ring shape, which is formed on the ocular fundus Ef of each of the left eye EL and the right eye ER, is displayed in the anterior ocular segment display areas 51L, 51R of FIG. 10.

The refraction measurement is carried out in accordance with a known procedure. That is, the ring-shaped light flux receiving system 33B projects a ring-shaped measuring pattern to the ocular fundus Ef of the eye E and forms the measuring pattern image Kr having a ring shape on the ocular fundus Ef (see FIG. 10). The image of the ocular fundus Ef with the measuring pattern image Kr is collected by the objective lens 31a and is imaged on the image pickup element 31g through the optical systems shared with the observation system 31. The image pickup element 31g detects the ring-shaped measuring pattern image Kr and outputs image signals to the controller 26 based on the obtained image.

Based on the received image signals, the controller 26 displays the measuring pattern images Kr for the left eye EL and the right eye ER in the anterior ocular segment display areas 51L, 51R. The controller 26 then analyzes the measuring pattern images Kr to calculate the spherical power S, the cylindrical power C, and the axis angle (cylinder axis angle) Ax of the eye E.

Figure 11:
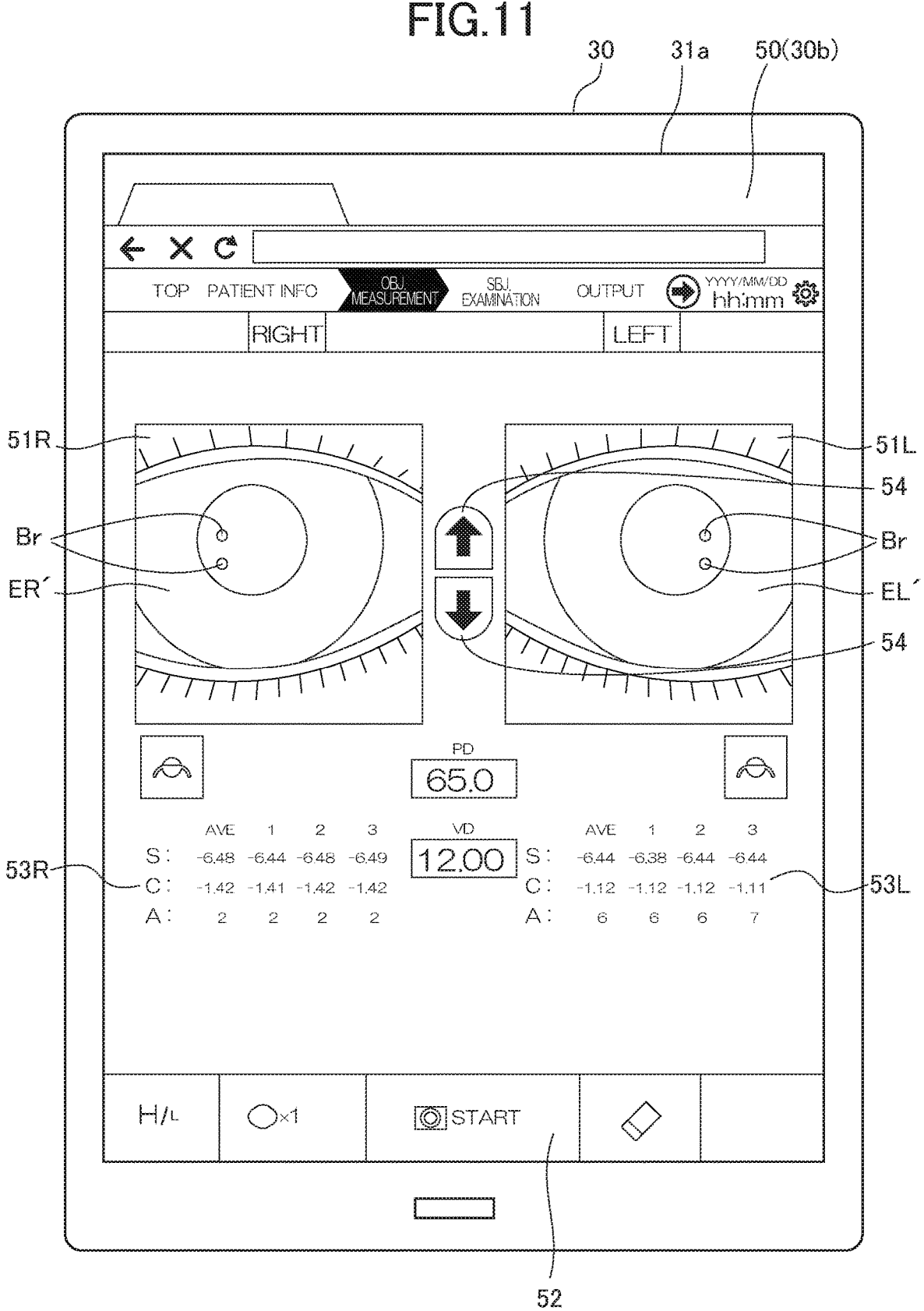
FIG. 11 is a view illustrating another example of image displayed on the display of the ophthalmologic apparatus of the embodiment.

Next, in Step S7, the controller 26 displays the calculated spherical power S, cylindrical power C, and the axis angle (cylinder axis angle) Ax for each of the left eye EL and the right eye ER in measurement result display areas 53L, 53R in the operation screen 50, as shown in FIG. 11. Additionally, the controller 26 displays the anterior ocular segment images EL', ER' of the left eye EL and the right eye ER in the anterior ocular segment display areas 51L, 51R. Through the above process, the refraction measurement of the eye to be examined E is completed.

Technical effects achieved by the ophthalmologic apparatus 10 of this embodiment will be described. As described above, the ophthalmologic apparatus 10 of the embodiment comprises the measurement optical system 24, the image pickup element (image obtaining part) 31g, the display 30, two of the cameras 40, 41, the driving mechanism 22, and the controller 26. The controller 26 acquires three-dimensional position information of the eye to be examined E based on two or more of images captured by the two or more of the cameras 40, 41 and calculates a moving amount of the measurement optical system 24 in the vertical direction and a moving amount of the measurement optical system 24 in the horizontal direction based on the acquired position information. The controller 26 then controls the driving mechanism 22 based on the calculated moving amounts to position the measurement optical system 24 with respect to the eye E, and displays the obtained anterior ocular segment image E on the display 30 while positioning the measurement optical system 24.

With this configuration, the positional relationship between the eye to be examined E and the measurement optical system 24 is accurately acquired three-dimensionally based on the images captured by the cameras 40, 41. Accurate alignment is thereby achieved in a broad range. Accordingly, positioning of the measurement optical system with respect to the eye to be examined E is appropriately achieved even when it is unable to specify the pupil center of the eye E due to a cataract eye. This allows the examiner to easily confirm the alignment and the condition of the eye E, and therefore allows to carry out the positioning swiftly and accurately. A proper measurement of characteristics of the eye to be examined is thereby achieved.

With the conventional configuration, the examiner needs to confirm the alignment using images captured by the cameras from oblique directions with respect to the optical axes. On the other hand, the controller 26 of the embodiment is configured to display the anterior ocular segment images E (i.e., front view of the eye) along the corresponding optical axes of the measurement optical systems 24 in real-time based on the image signals outputted from the image pickup element 31g. Therefore, the examiner is able to precisely confirm the accuracy of the alignment.

This configuration also allows the examiner to precisely confirm the state of the eyes E using the real-time images (i.e., live images) during the alignment. For example, the examiner is able to confirm the following states (1) to (4) of the eyes to be examined E, advantageously: (1) Failure of fixation, (2) Having heterophoria, (3) Having blepharoptosis, and (4) Constriction of pupil.

If the eye to be examined E is under one of the above states, it is difficult to properly perform the alignment. By properly recognizing the states of the eyes E, it is possible to specify the cause of troubles quickly and clearly when the alignment fails, for example. Hence, the examiner is able to eliminate the cause of troubles by instructing the patient to fix his/her eyes and/or by forcibly opening the eyelid of the patient, for example. As a result, the alignment and the measurement of the characteristics of the eyes to be examined E is achieved quickly and accurately.

Additionally, the examiner is able to confirm the conditions of the eyes to be examined E during the measurement since the anterior ocular segment images E' are displayed on the operation screen 50 while the measurement of the characteristics of the eyes E is carried out. As a result, it is possible to improve the accuracy of the measurement and to facilitate specifying the cause of troubles when the measurement fails.

In the embodiment, the ophthalmologic apparatus 10 comprises a pair of the measurement optical systems 24L, 24R each of which respectively corresponds to a left eye EL and a right eye ER to be examined. Each of the measurement optical systems 24L, 24R comprises the image pickup elements 31g and the two or more of the cameras 40, 41. The controller 26 displays the anterior ocular segment images EL', ER' of the left eye EL and the right eye ER on the display 30. With this configuration, in addition to the states (1) to (4) the examiner is able to confirm the following states (5) to (7) of the eyes to be examined E: (5) Failure of binocular vision, (6) Having suppression of the eye E, and (7) Having head tilt. By properly recognizing the conditions of the eyes E, it is possible to further improve the accuracy of the alignment and of the measurement. Particularly, the measurement accuracy with binocular vision significantly improves since the fixation of the eyes, which is an important factor for the measurement with binocular vision, is ensured with the above configuration.

In the embodiment, the display 30 comprises a touch-panel inputter 30b. The touch-panel inputter 30b is superimposingly arranged on a display surface 30a on which the anterior ocular segment image E is displayed. The controller 26 successively displays the anterior ocular segment image E on the display surface 30a while positioning the measurement optical system 24 in accordance with commands inputted through the inputter 30b. With this configuration, the examiner is able to recognize and confirm the condition of the alignment while carrying out the alignment operation. As a result, the operability of the ophthalmologic apparatus 10 (i.e., controller 26) significantly improves. Additionally, the examiner is able to quickly confirm completion of the alignment or to precisely specify the cause of troubles when the alignment fails.

In the embodiment, the controller 26 extracts a feature point of the eye E based on the images captured by the two or more of the cameras 40, 41 and calculates a distance from the feature point to each of the two or more of the cameras 40, 41. The controller 26 further calculates the three-dimensional position information of the eye E based on the calculated distances and a predetermined mutual distance between the two or more of the cameras 40, 41. With this configuration, the three-dimensional position information of the eyes to be examined E is acquired more accurately such that the accuracy of the alignment further improves.

In the embodiment, the ophthalmologic apparatus 10 further comprises an arm 14 that supports the measurement optical system 24. The driving mechanism 22 is suspended by the arm 14, and the measurement optical system 24 is suspended by the driving mechanism 22. In this configuration, the arm 14 improves the freedom of arranging the driving mechanism 22. This allows a space to be secured in front of the patient while enabling the alignment of the measurement optical system 24 in X, Y, and Z directions with the driving mechanism 22. As a result, the ophthalmologic apparatus 10 reduces feeling of oppression of the patient.

Although the present disclosure has been described in terms of an exemplary embodiment, it should not be limited thereto. It should be appreciated that variations or modifications may be made in the embodiment described by persons skilled in the art without departing from the scope of the present invention as defined by the following claims.

For example, the disclosure describes an example of the operation for measuring the ocular refractive power as well as the operation screen 50 for the measurement displayed on the display surface 30a. However, it should not be limited to the example. The described operation is applicable to, for example, corneal shape measurement (i.e., kerato measurement), intraocular pressure measurement, fundus photographing, and OCT photographing. It is also applicable to the subjective refraction measurement such as far-sight examination, near-sight examination, contrast examination, and glare test, as well as the subjective examination such as visual-field inspection. An operation screen corresponding to the above-listed measurement is displayed on the display 30, and the anterior ocular segment image E' (i.e., front view) of the eye to be examined E is displayed on the operation screen. Accordingly, the examiner is able to properly observe the state of the alignments and the conditions of the eye to be examined E while carrying out the measurement.

The ophthalmologic apparatus of the embodiment comprises the left-eye measurement optical system 24L and the right-eye measurement optical system 24R to measure the characteristics of the eye to be examined E with binocular vision. However, it should not be limited thereto. The ophthalmologic apparatus 10 of the disclosure is applicable for carrying out the measurement with monocular vision. That is, the ophthalmologic apparatus 10 of the disclosure allows the alignment and the measurement of the characteristics of the eye to be examined E quickly and accurately while allowing the examiner to observe the anterior ocular segment image E (i.e., front view of the eye) with monocular vision. It should be noted that when the ophthalmologic apparatus 10 comprises a single measurement optical system 24 to carry out the measurement with monocular vision, the deflection members may be omitted, as illustrated in FIG. 5.

What is claimed is:

1. An ophthalmologic apparatus comprising:
a measurement optical system configured to acquire information of an eye to be examined;
an image obtaining part configured to obtain an anterior ocular segment image of the eye on an optical axis of the measurement optical system;
a display configured to display the anterior ocular segment image;
two or more cameras, each being configured to capture an image of an anterior ocular segment of the eye from a different direction;
a driving mechanism configured to move the measurement optical system in a vertical direction and a horizontal direction; and
a controller,
wherein:
the controller is configured to acquire three-dimensional position information of the eye based on the images captured by the two or more cameras and calculate a moving amount of the measurement optical system in the vertical direction and a moving amount of the measurement optical system in the horizontal direction based on the three-dimensional position information;

the controller is configured to control the driving mechanism based on the moving amount of the measurement optical system in the vertical direction and the moving amount of the measurement optical system in the horizontal direction to position the measurement optical system with respect to the eye;

the display comprises a touch-panel inputter, the touch-panel inputter being superimposingly arranged on a display surface on which the anterior ocular segment image is displayed; and the controller is configured to successively display the anterior ocular segment image obtained by the image obtaining part on the display while positioning the measurement optical system in accordance with a command for alignment inputted through the touch-panel inputter.

2. The ophthalmologic apparatus according to claim 1, wherein:

the eye to be examined is a left eye or a right eye;

the ophthalmologic apparatus comprises a pair of the measurement optical, a first of the pair of the measurement optical systems corresponding to the left eye and a second of the pair of the measurement optical systems corresponding to the right eye;

each of the pair of the measurement optical systems comprises the image obtaining part and the two or more cameras; and the controller is configured to display the anterior ocular segment image of the left eye and the anterior ocular segment image of the right eye on the display.

3. The ophthalmologic apparatus according to claim 2, wherein, for each of the left eye and the right eye:

the controller is configured to extract a feature point of the eye based on the images captured by the two or more cameras and calculate a distance from the feature point to each of the two or more cameras; and the controller is configured to calculate the three-dimensional position information of the eye based on the distances which have been calculated and a predetermined mutual distance between the two or more cameras.

4. The ophthalmologic apparatus according to claim 1, wherein:

the controller is configured to extract a feature point of the eye based on the images captured by the two or more cameras and calculate a distance from the feature point to each of the two or more cameras; and the controller is configured to calculate the three-dimensional position information of the eye based on the distances which have been calculated and a predetermined mutual distance between the two or more cameras.

5. The ophthalmologic apparatus according to claim 1, further comprising a supporter that supports the measurement optical system, wherein:

the driving mechanism is suspended by the supporter; and the measurement optical system is suspended by the driving mechanism.

6. The ophthalmologic apparatus according to claim 1, further comprising an examiner's controller that comprises the display, wherein the touch-panel inputter is an operation screen that comprises an anterior ocular segment display area.

7. The ophthalmologic apparatus according to claim 6, wherein the examiner's controller is a mobile terminal.

8. The ophthalmologic apparatus according to claim 6, wherein the controller is configured to display the anterior ocular segment image in the anterior ocular segment display area of the operation screen based on an image signal.

9. A measurement method of an eye to be examined, the measurement method comprising:

obtaining an anterior ocular segment image of the eye on an optical axis of a measurement optical system;

capturing two or more images of an anterior ocular segment of the eye with two or more cameras from different directions;

acquiring three-dimensional position information of the eye based on the two or more images that have been captured;

calculating a moving amount of the measurement optical system in a vertical direction and a moving amount of the measurement optical system in a horizontal direction based on the three-dimensional position information;

positioning the measurement optical system with respect to the eye based on the moving amount of the measurement optical system in the vertical direction and the moving amount of the measurement optical system in the horizontal direction; and successively displaying the anterior ocular segment image which has been obtained on a display while positioning the measurement optical system in accordance with a command for alignment inputted through a touch-panel inputter, wherein the display comprises the touch-panel inputter, the touch-panel inputter being superimposingly arranged on a display surface on which the anterior ocular segment image is displayed.

10. The measurement method according to claim 9, wherein:

the display is provided in an examiner's controller; and the touch-panel inputter is an operation screen that comprises an anterior ocular segment display area.

11. The measurement method according to claim 10, wherein the examiner's controller is a mobile terminal.

12. The measurement method according to claim 10, wherein successively displaying the anterior ocular segment image on the display comprises displaying the anterior ocular segment image in the anterior ocular segment display area of the operation screen based on an image signal.

* * * * *